(12) United States Patent
Jones et al.

(10) Patent No.: US 7,156,871 B2
(45) Date of Patent: Jan. 2, 2007

(54) EXPANDABLE STENT HAVING A STABILIZED PORTION

(75) Inventors: Donald K. Jones, Lauderhill, FL (US); Marc Ramer, Weston, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

(21) Appl. No.: 10/975,842

(22) Filed: Oct. 28, 2004

(65) Prior Publication Data

US 2006/0095111 A1    May 4, 2006

(51) Int. Cl.
A61F 2/06    (2006.01)

(52) U.S. Cl. .................................. 623/1.13; 623/903

(58) Field of Classification Search ............... 623/1.13, 623/1.35, 1.38, 903
See application file for complete search history.

(56) References Cited

U.S. PATENT DOCUMENTS

| | | | |
|---|---|---|---|
| 4,743,252 A | 5/1988 | Martin, Jr. et al. | |
| 5,064,435 A | 11/1991 | Porter | |
| 5,100,429 A | 3/1992 | Sinofsky et al. | |
| 5,609,628 A | 3/1997 | Keranen | |
| 5,665,063 A | 9/1997 | Roth et al. | |
| 5,702,418 A | 12/1997 | Ravenscroft | |
| 5,713,917 A | 2/1998 | Leonhardt et al. | |
| 5,749,919 A | 5/1998 | Blanc | |
| 5,755,773 A | 5/1998 | Evans et al. | |
| 5,769,884 A | 6/1998 | Solovay | |
| 5,921,954 A | 7/1999 | Mohr, Jr. et al. | |
| 5,951,599 A | 9/1999 | McCrory | |
| 6,004,261 A | 12/1999 | Sinofsky et al. | |
| 6,030,414 A | 2/2000 | Taheri | |
| 6,102,938 A | 8/2000 | Evans et al. | |
| 6,254,628 B1 | 7/2001 | Wallace et al. | |
| 6,290,673 B1 | 9/2001 | Shanley | |
| 6,395,018 B1 | 5/2002 | Castaneda | |
| 6,497,722 B1 | 12/2002 | Von Oepen et al. | |
| 6,524,335 B1 | 2/2003 | Hartley et al. | |
| 6,569,195 B1 | 5/2003 | Yang et al. | |
| 6,605,111 B1 | 8/2003 | Bose et al. | |
| 6,673,106 B1 | 1/2004 | Mitelberg et al. | |
| 6,833,003 B1 | 12/2004 | Jones et al. | |
| 2001/0000802 A1* | 5/2001 | Soykan et al. | 623/1.13 |
| 2002/0035394 A1 | 3/2002 | Fierens et al. | |
| 2002/0055769 A1 | 5/2002 | Wang | |
| 2002/0062147 A1 | 5/2002 | Yang | |
| 2002/0072790 A1 | 6/2002 | McGuckin, Jr. et al. | |
| 2002/0072792 A1 | 6/2002 | Burgermeister et al. | |
| 2002/0128706 A1 | 9/2002 | Osypka | |
| 2002/0143385 A1* | 10/2002 | Yang | 623/1.13 |
| 2002/0193872 A1 | 12/2002 | Trout, III et al. | |

(Continued)

OTHER PUBLICATIONS

U.S. Appl. No. 10/696,667, filed Oct. 29, 2003, Pomeranz et al.

(Continued)

*Primary Examiner*—Eduardo C. Robert
*Assistant Examiner*—Thomas J. Sweet
(74) *Attorney, Agent, or Firm*—Henry W. Collins

(57) ABSTRACT

An expandable stent having a covering which exhibits the characteristic of being normally dissolvable in blood, but upon being activated, becomes inert to blood. The stent may be placed across the neck of an aneurysm to seal the aneurysm and thereafter the portion of the covering of the stent across the neck of the aneurysm is activated to become inert to blood and the balance of the covering dissolves to permit blood to flow to adjacent vessels.

4 Claims, 4 Drawing Sheets

U.S. PATENT DOCUMENTS

| | | |
|---|---|---|
| 2002/0193873 A1 | 12/2002 | Brucker et al. |
| 2003/0074049 A1 | 4/2003 | Hoganson et al. |
| 2003/0109917 A1 | 6/2003 | Rudin et al. |
| 2003/0135265 A1 | 7/2003 | Stinson |
| 2003/0139802 A1 | 7/2003 | Wulfman et al. |
| 2003/0153972 A1 | 8/2003 | Helmus |
| 2003/0199993 A1* | 10/2003 | Gellman et al. ......... 623/23.75 |
| 2003/0208256 A1 | 11/2003 | DiMatteo et al. |
| 2004/0006381 A1 | 1/2004 | Sequin et al. |
| 2004/0044396 A1 | 3/2004 | Clerc et al. |
| 2004/0098076 A1* | 5/2004 | Rolando et al. ............. 623/1.1 |

OTHER PUBLICATIONS

U.S. Appl. No. 10/976,412, filed Oct. 28, 2004, Jones et al.
European Search Report re: EP05256709 dated Mar. 21, 2006.

* cited by examiner

EXPANDABLE STENT HAVING A STABILIZED PORTION

BACKGROUND OF INVENTION

1. Field of the Invention

The present invention relates to intravascular stents and methods of treating aneurysms, and more particularly, this invention relates to a covered stent which may be modified to seal the neck of an aneurysm located adjacent to perforating blood vessels while permitting blood to flow through the perforating blood vessels, and methods of use thereof.

2. Description of the Prior Art

Expandable stents are widely used in the treatment of vascular diseases. Typically, a stent is inserted into a stenosed blood vessel after an angioplasty to prevent the restenosis of the blood vessels. Expandable stents are also used as aneurysm covers. When a stent is placed across an aneurysm, the blood flow into the aneurysm is decreased. Decreased blood flow within an aneurysm promotes the formation of a thrombus within the aneurysm which ultimately aids in protecting the aneurysm from further expansion or rupture.

Optimally, a covered stent is positioned across an aneurysm to completely restrict the blood flow into the aneurysm. Such covered stents, typically covered with a material such as PTFE provide suitable aneurysm covers; however, these stents have certain limitations. For example, covered stents impede blood flow into or out of branching or perforating blood vessels. Thus, a covered stent may not be suitable for treating an aneurysm at or near a bifurcated blood vessel or a blood vessel having perforating vessels adjacent to the aneurysm.

Several patents and patent applications disclose covered stents with various modifications which tend to avoid these limitations inherent with typical covered stents. For example, U.S. Pat. No. 6,030,414, entitled "Variable Stent And Method For Treatment Of Arterial Disease," discloses a covered stent having predetermined and sized lateral openings for the treatment of arterial disease at or around the intersection of multiple arteries; U.S. Pat. No. 6,497,722, entitled "Method And Apparatus For In-Vivo Tailored Stents Indicated For Use In Tortuous Anatomy," discloses a stent having a side opening to allow unimpeded blood flow to a branching vessel at the point of stenting; and, U.S. Patent Application Publication No. 2003/0074049, entitled "Covered Stents And Systems For Deploying Covered Stents," discloses a covered stent which may be perforated in order to allow blood flow into a side branch or bifurcated vessel.

Also, U.S. patent application Ser. No. 10/696,667, filed on Oct. 29, 2003, assigned to the same assignee as the subject patent application, discloses a covered stent for treating an aneurysm which includes a skeletal stent structure with removable slat members to permit blood to flow through a bifurcated blood vessel. Upon deployment, one or more of the slats may be removed to allow blood to flow through portions of the stent structure while others of the slats are left in place to seal the neck of an adjacent aneurysm. This patent application is made of record in the subject patent application and is hereby incorporated and made a part of the subject application.

SUMMARY OF THE INVENTION

In accordance with one aspect of the present invention there is provided an aneurysm treatment device including an expandable stent which takes the form of a small diameter skeletal tubular member having a thin wall which includes a plurality of cells which are formed by a plurality of interconnected strut members. A covering extends over at least a portion of the expandable stent. The covering exhibits the characteristic of being normally dissolvable when in contact with bodily fluids, but upon applying an activating agent to the covering, the covering becomes inert to bodily fluids. The stent may take the form of a metallic skeletal tubular member, and the covering may take the form of a polymer which is comprised of a material which polymerizes when it comes into contact with the activating agent. More particularly, the covering may take the form of sodium alginate and the activating agent may take the form of a solution comprised in calcium ions. Preferably, the covering is a thin film of sodium alginate material disposed on the outer surface of the expandable stent.

In accordance with another aspect of the present invention, there is provided a method of treating an aneurysm comprising the method steps of providing an expandable covered stent including a skeletal tubular member having a covering disposed onto the skeletal tubular member in which the covering is formed of a material which normally dissolves when in contact with bodily fluids, such as blood. The method also includes the steps of inserting the covered stent into a blood vessel of a patient, advancing the covered stent until the covering of the stent is aligned with and is adjacent to the neck of an aneurysm in the blood vessel, expanding the skeletal tubular member so that a portion of the covering extends across the neck of the aneurysm, and applying an activating element to that portion of the covering which extends across the neck of the aneurysm to cause that portion of the covering to become inert to bodily fluids thereby preventing that portion of the covering from dissolving when in contact with bodily fluids. That portion of the covering serves to provide a seal across the neck of the aneurysm. The balance of the covering is then permitted to dissolve when in contact with bodily fluids in order to allow blood to flow through adjacent blood vessels, such as perforating blood vessels.

In accordance with still another aspect of the present invention there is provided a method for treating an aneurysm comprising the method steps of inserting a drug delivery catheter into the vasculature of a patient and advancing the distal tip of the drug delivery catheter into an aneurysm to be treated, providing an expandable covered stent including a skeletal tubular member having a covering disposed onto the skeletal member. The covering is formed of a material which normally dissolves when in contact with bodily fluid, such as blood, but upon being activated becomes inert to bodily fluid. The method also includes the step of inserting the covered stent into the blood vessel of a patient, advancing the covered stent until the covering of the stent is aligned with and is adjacent to the neck of an aneurysm in the blood vessel, expanding the skeletal tubular member so that a portion of the covering extends across the neck of the aneurysm, applying an activating agent through the drug delivery catheter into the aneurysm to thereby cause contact between the activating agent and the portion of the covering across the neck of the aneurysm to thereby stabilize that portion of the covering to prevent dissolution of that portion when in contact with bodily fluid, and then permitting the balance of the covering to dissolve while in contact with blood in order to permit blood to flow into adjacent blood vessel.

DESCRIPTION OF THE PREFERRED EMBODIMENT

Figure 1:
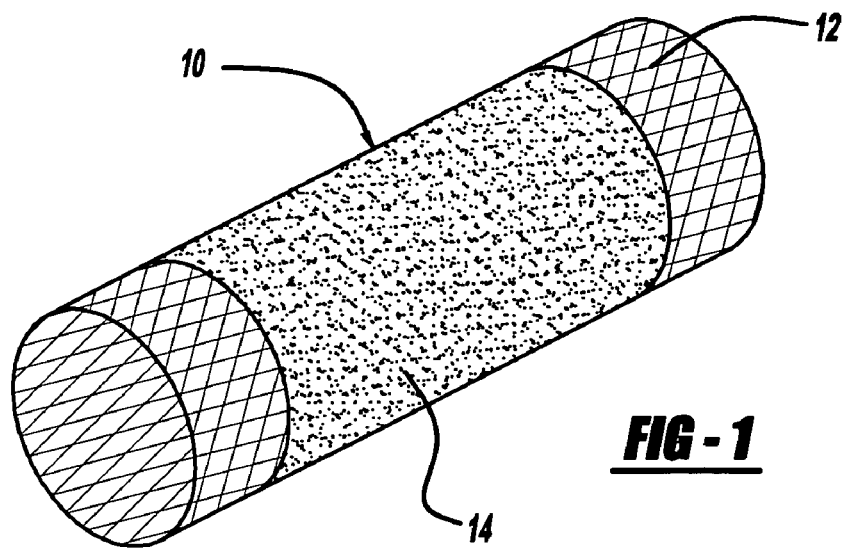
FIG. 1 is an enlarged oblique view of a covered stent device comprised of an expandable skeletal support member and a outer covering which extends over a portion of the support member.

FIG. 1 illustrates an expandable covered stent 10 which may be used to treat an aneurysm, such as an aneurysm within the brain, occurring in a blood vessel at or near a branching vessel, such as a perforating vessel. In the preferred embodiment of the present invention, the covered stent 10 is comprised of an expandable skeletal stent 12 and a unique outer covering 14 disposed on the outer surface of the skeletal stent 12.

More particularly, the skeletal stent 12 includes a plurality of cells which are formed by a plurality of interconnected strut members to thereby define a structure which may be placed into a vessel and after being properly aligned may then be expanded. The skeletal stent 12 may either take the form of a balloon expandable stent or a self-expanding stent. An example of such a self expanding stent is disclosed in U.S. Pat. No. 6,673,106, entitled, "Intravascular Stent Device," and an example of a stent and stent deployment system is disclosed in U.S. patent application Ser. No. 10/365,288, entitled, "Expandable Stent And Delivery System," filed on Feb. 12, 2003. This patent and patent application are assigned to the same assignee as the present patent application and are hereby made of record and are incorporated by reference into the present patent application.

The outer covering 14 preferably takes the form of a polymer which is normally dissolvable in bodily fluid, such as blood, but which upon activation by an activating agent, polymerizes and becomes inert to bodily fluids, such as blood. A suitable activating or polymerizing agent is a solution of calcium ions. A suitable material for the outer covering is sodium alginate which may be bonded to the surface of the skeletal stent 12. The skeletal stent 12, as will be subsequently described in more detail, serves to cover the neck of the aneurysm.

Figure 2:
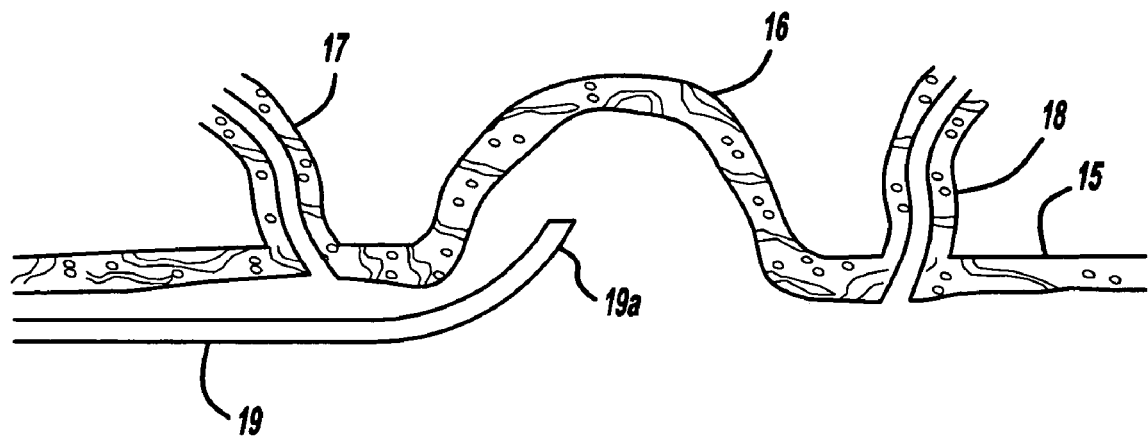
FIG. 2 is an enlarged elevational view of a blood vessel showing an aneurysm and adjacent perforating blood vessels with a drug infusion catheter inserted into the aneurysm.

FIG. 2 illustrates a blood vessel 15 showing an aneurysm 16 formed in the wall of the vessel at a position in the vicinity to two small perforating blood vessels 17, 18. Also, illustrated is a drug infusion catheter 19 which has been introduced into the vasculature of the body and has been positioned such that the distal tip 19a extends into the aneurysm 16.

Figure 3:
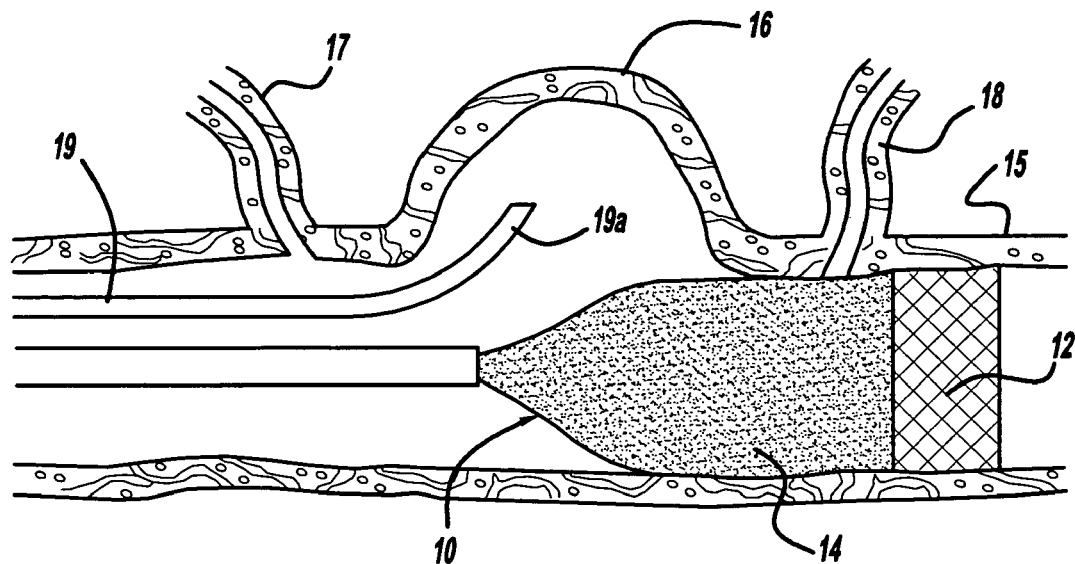
FIG. 3 is an enlarged elevational view illustrating the partial deployment of a covered stent.
Figure 4:
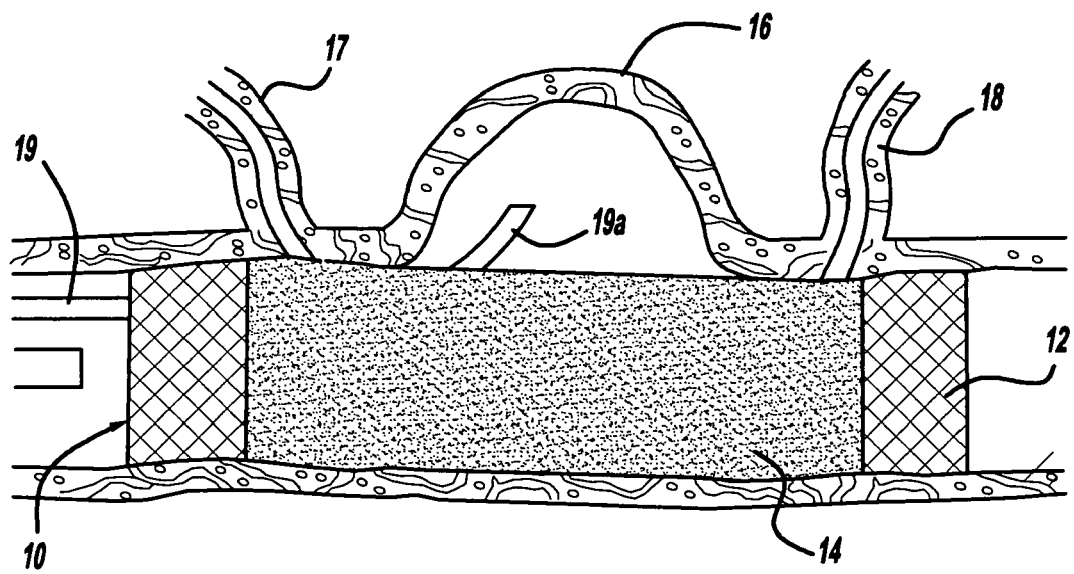
FIG. 4 is an enlarged elevational view illustrating the full deployment of a covered stent prior to activation.

FIGS. 3 and 4 illustrate the covered stent 10 as it is deployed by expansion such that the outer covering 14 extends across the neck of an aneurysm 16. Also, since the aneurysm 16 occurs at a location adjacent to perforating vessels 17, 18, which serve to feed other organs of the body, placement of the covered stent such that the outer covering 14 covers the neck of the aneurysm 16 also causes the covering to obstruct the flow of blood to the perforating vessels 17, 18. Aneurysms frequently occur at the location near branching vessels, therefore, it should be noted that one of the major advantages of the present invention is that the covered stent 10 may serve to provide a covering for the aneurysm 16 and at the same time be modified to allow blood to flow to branching, or perforating vessels 17, 18. This modification will be explained in more detail relative to the following drawings.

Figure 5:
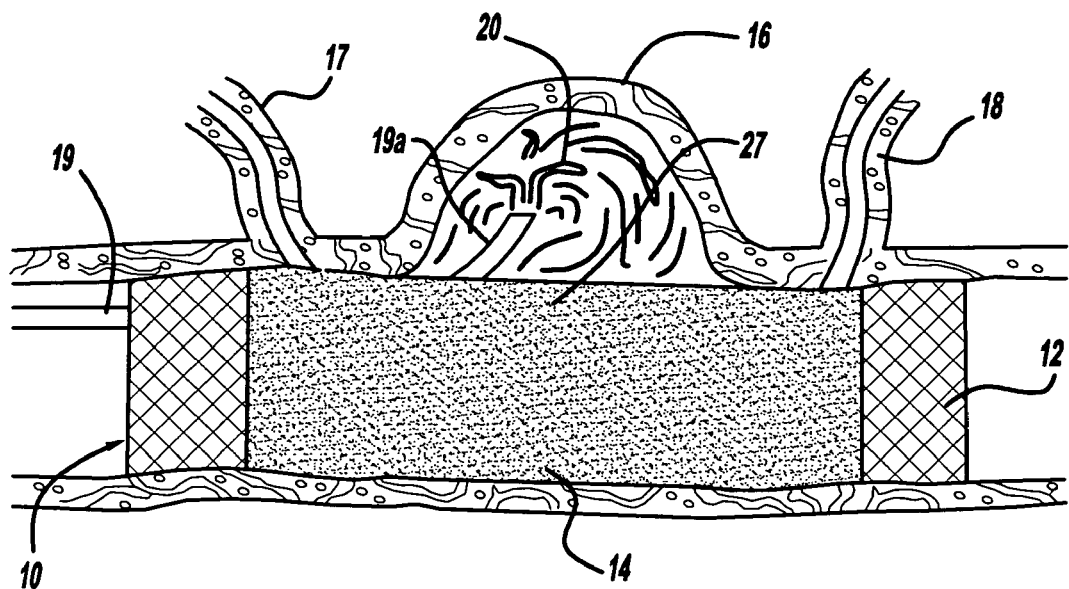
FIG. 5 is an enlarged elevational view of the deployed covered stent with an activated agent being applied to the aneurysm.

FIG. 5, is somewhat similar to FIG. 2, but illustrates the covered stent 10 positioned so that the outer covering 14 occludes both the aneurysm 16 and the adjacent perforating vessels 17, 18. Once the covered stent 10 is properly placed, an activating agent 20 is injected through the drug delivery catheter 19 and into the aneurysm. The activating agent then replaces blood within the aneurysm and comes into contact with that portion 22 of the covering which extends across the neck of the aneurysm 16.

Figure 6:
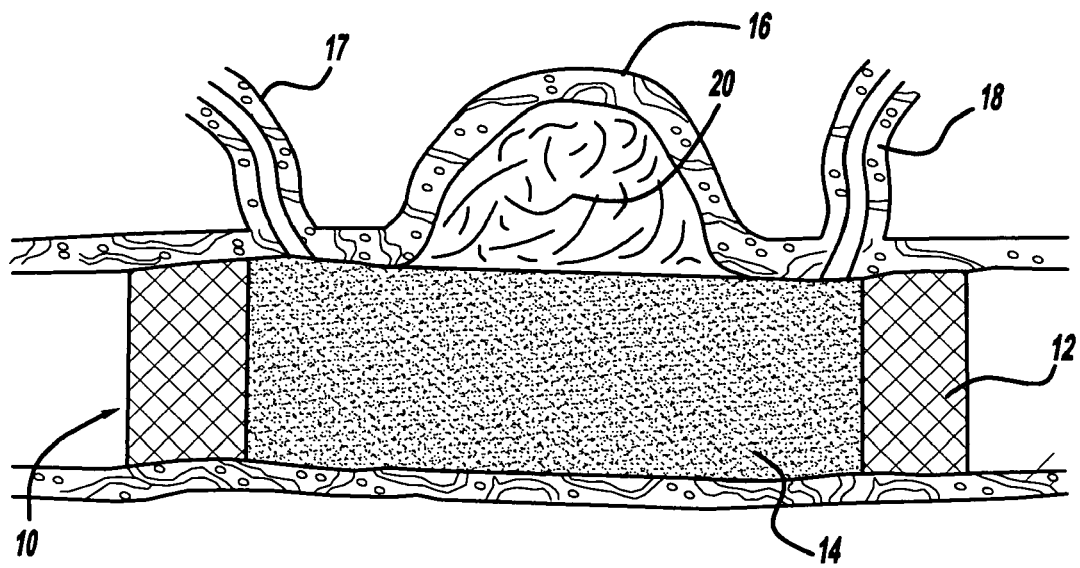
FIG. 6 is an enlarged elevational view of the deployed covered stent showing contact between the activating agent and the covered stent after removal of the drug infusion catheter; and, FIG. 7 is an enlarged elevational view illustrating the covered stent after stabilization of the portion of the covering across the neck of the aneurysm and after dissolution of the remaining portion of the covering.

FIG. 6, which is similar to FIG. 5, illustrates the removal of the drug delivery catheter 19 and also illustrates the contact between the activating agent 20 and portion 22 of the covering which extends across the aneurysm 16. As indicated, the covering is formed of a material, such as a thin film of sodium alginate, which when contacted by an activating agent, such as a solution of calcium ions, becomes polymerized and stabilizes.

Figure 7:
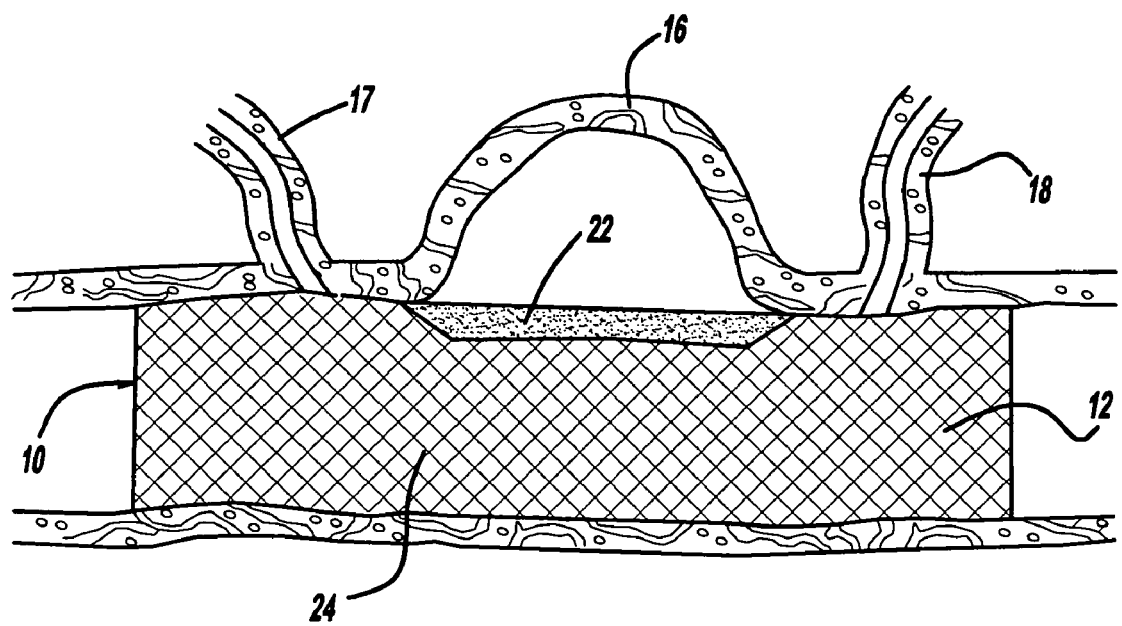

FIG. 7 illustrates the covered stent 10 after the portion 22 of the covering across the neck has become polymerized to thereby seal the neck of the aneurysm 16. The balance of the covering 24, i.e. that portion not in contact with the activating agent, has dissolved to expose the skeletal stent 12 thereby permitting blood to flow through the exposed porous structure to allow blood to flow into the perforating blood vessels 17, 18.

Accordingly, with the covered stent of the present invention it is possible to seal the neck of an aneurysm with obstructing adjacent, or perforating, blood vessels. If three adjacent blood vessels are left obstructed, injury or loss of organs might well occur.

A novel medical device and method to treat an aneurysm near branching, or perforating, blood vessels has been disclosed. Although a preferred embodiment of the present invention has been described, it should be understood that various modifications, such as, for example stabilizing a portion of the covering by an electrical or electrolytic process, by a heating process or by other processes may be made by one skilled in the art without departing from the scope of the claims which follow.

That which is claimed is:

1. A method of treating an aneurysm comprising:
   providing an expandable covered stent including a skeletal tubular member having a covering disposed onto the skeletal tubular member, said covering formed of a material which normally dissolves when in contact with blood;
   inserting said covered stent into a blood vessel of a patient;

advancing said covered stent until the covering of the stent is aligned with and is adjacent to a neck of an aneurysm in the blood vessel;

expanding said skeletal tubular member so that a portion of said covering extends across the neck of the aneurysm; and, applying an activating agent to said portion of said covering to cause said portion of said covering to stabilize to thereby prevent it from dissolving when in contact with blood to thereby provide a seal across the neck of the aneurysm; and, permitting the balance of the covering to dissolve while in contact with blood in order to permit blood to flow into adjacent blood vessels.

2. A method of treating an aneurysm as defined in claim 1, wherein the covering is sodium alginate and the activating element is a solution containing calcium ions.

3. A method of treating an aneurysm comprising:

inserting a drug delivery catheter into the vasculature of a patient and advancing the distal tip of the drug delivery catheter into an aneurysm to be treated;

providing an expandable covered stent including a skeletal tubular member having a covering disposed onto the skeletal tubular member, said covering formed of a material which normally dissolves when in contact with blood;

inserting said covered stent into a blood vessel of a patient;

advancing said covered stent until the covering of the stent is aligned with and is adjacent to a neck of an aneurysm in the blood vessel;

expanding said skeletal tubular member so that a portion of said covering extends across the neck of the aneurysm;

applying an activating agent through said drug delivery catheter into the aneurysm to thereby cause contact between said activating agent and said portion of said covering to thereby stabilize said portion to prevent dissolution of said portion when in contact with blood; and, permitting the balance of the covering to dissolve while in contact with blood in order to permit blood to flow into adjacent blood vessels.

4. A method of treating an aneurysm as defined in claim 3, wherein said covering takes the form of sodium alginate and the activating agent takes the form of a solution comprising calcium ions.

* * * * *